United States Patent [19]
Wier

[11] Patent Number: 5,773,232
[45] Date of Patent: Jun. 30, 1998

[54] METHODS FOR MEASUREMENT OF LYMPHOCYTE FUNCTION

[75] Inventor: Majorie L. Wier, Columbia, Md.

[73] Assignee: Biotechnology Transfer, Inc., Columbia, Md.

[21] Appl. No.: 928,392

[22] Filed: Sep. 12, 1997

Related U.S. Application Data

[63] Continuation of Ser. No. 621,878, Mar. 26, 1996, abandoned.

[51] Int. Cl.[6] .................... G01N 33/53; G01N 33/553; C12Q 1/70; C12Q 1/24
[52] U.S. Cl. .................... 435/7.24; 435/5; 435/7.9; 435/30; 436/526; 436/548
[58] Field of Search .................... 435/5, 7.24, 7.9, 435/30; 436/526, 548

[56] References Cited

U.S. PATENT DOCUMENTS

| | | | |
|---|---|---|---|
| 4,483,928 | 11/1984 | Suzuta et al. | 436/519 |
| 4,665,022 | 5/1987 | Schaeffer et al. | 435/7 |
| 4,778,750 | 10/1988 | Gottlieb | 435/5 |
| 5,095,097 | 3/1992 | Hermentin et al. | 530/391.5 |
| 5,112,735 | 5/1992 | Albertini | 435/6 |
| 5,340,749 | 8/1994 | Fujiwara et al. | 436/526 |
| 5,344,755 | 9/1994 | Shearer et al. | 435/5 |
| 5,374,531 | 12/1994 | Jensen | 435/7.24 |
| 5,385,822 | 1/1995 | Melnicoff et al. | 435/5 |
| 5,395,751 | 3/1995 | McMichael et al. | 435/5 |

OTHER PUBLICATIONS

Petty, R.D., et al., *J Biolumin Chemilumin*, 1995; 10:29–34 "Comparison of MTT and ATP–Based Assays for the Measurement of Viable Cell Number".

Groeneveld, K., et al, *JIFCC*, vol. 6, Issue 3, Jun. 1994 "Blood T–cell Subsets in Health and Disease".

Coe Clough, N.E., et al, Leading Edge of Medicine—A Review, *JAVMA*, vol. 206, No. 8, Apr. 15, 1995, "Methods for assessing cell–mediated immunity in infectious disease resistance and in the development of vaccines".

Ishizaka, et al. : Evaluation of proliferative response of lymphocytes . . . : J. Immun. Meth.: vol. 72: pp. 127–132, 1984.

*Primary Examiner*—Lynette F. Smith
*Assistant Examiner*—Brett L. Nelson
*Attorney, Agent, or Firm*—Whitham, Curtis & Whitham

[57] ABSTRACT

A method for measuring the responses of sets or subsets of lymphocytes to mitogens or antigens in a sample is disclosed comprising incubating a population of cells with a mitogen or antigen, separating the desired subset of cells by means of the interaction of a specific binding reagent that is attached to the solid phase with a cell surface determinant that is present on the cell subset of interest, lysing the separated cells, and measuring an intracellular component that is increased if the cells have responded to the stimulus. The method provides a convenient, simple, and reliable method for measuring immune function in a variety of conditions.

19 Claims, 2 Drawing Sheets

5,773,232

METHODS FOR MEASUREMENT OF LYMPHOCYTE FUNCTION

CROSS-REFERENCE TO RELATED APPLICATIONS

This application is a continuation application of U.S. Ser. No. 08/621,878, filed Mar. 26, 1996, now abandoned, and the complete contents of that application are herein incorporated by reference.

The U.S. Government has a nonexclusive, nontransferable, irrevocable paid-up license to practice or have practiced this invention for or on its behalf as provided for by the terms of Contract Number DAMD17-95-C-5057 awarded by the U.S. Department of the Army.

FIELD OF THE INVENTION

The invention relates to methods for measuring the function of lymphocytes and their responses to mitogens or specific antigens. The methods are suitable for measurement of the responses of T lymphocytes when they are a subpopulation of cells, and also for measuring the function of specific subsets of T lymphocytes, each subpopulation or subset of a subpopulation having characteristic determinants on their cell surface. The invention also relates to test kits used in performing such methods. The methods of the invention facilitate screening of complex biological fluids, such as whole blood, by means of incubating a sample of the fluid with a mitogen or antigen, separating the selected subset of interest, e.g., via affinity separation, and detecting the presence of an internal cellular component, advantageously ATP, that is increased as a result of the response.

BACKGROUND OF THE INVENTION

The immune system is central to control of infectious diseases and cancer. Lymphocytes, a class of white blood cells, are critical cell types that are responsible for the activities of the immune system. Lymphocytes are divided into two major categories, T lymphocytes and B lymphocytes. Overall assessment of the function of the immune systems and, in particular, lymphocytes is important in assessment of immunodeficiency caused by: genetic factors, infectious disease such as (HIV), drugs following transplantation, stress, aging, or nutritional deprivation.

Lymphocytes express receptors on the cell surface that bind with specific antigens or epitopes. Exposure to the antigen results in expansion in the population of the lymphocytes that are reactive to that antigen. Measurement of the response of the immune system to a specific antigen can be useful in diagnosis of infectious disease, hypersensitivity to certain agents, exposure to immunologically reactive drugs, or response to vaccination.

The function of B lymphocytes or their response to specific antigen can be assessed by measuring the level of specific antibody in bodily fluids such as blood, saliva or urine. The function of T lymphocytes or their response to specific antigens is more difficult to measure. Measurement of the functions of T lymphocytes or T cells is complicated by a number of factors. First, there are several different subsets of T cells with different functions. These subsets have been classified in part by the expression of characteristic cell surface markers and in part by a variety of functional assays including measurement of cytokines. Second, T cells respond to antigens only when they are presented by other cells in the context of major histocompatibility antigens on the surface of the presenting cell. Third, many of the functions of T cells depend on cell-cell contact with effector cells or the functions are fairly localized. Current methods for measuring immune function are tedious, time consuming, and poorly adapted to the clinical laboratory setting.

Methods that are currently used for measurement of immune function include: methods based on counting the number of T cells or different subsets; methods based on measuring the proliferation of lymphocytes, methods based on measurement of cytotoxic activity or secretion of cytokines, and methods used in vivo such as skin tests and adoptive transfer. These methods are described in detail in the literature ( see for example Groeneveld et al., Journal of the International Federation of Clinical Chemistry, 6: 84–94; 1994; Clough and Roth, JAVMA 206:1208–1216, 1995).

The methods most commonly used in the clinical laboratories are based on counting the number of T cells or subsets. A variety of techniques have been described including immunofluorescence microscopy, immunocytochemistry, enzyme immunoassay, and flow cytometry. Flow cytometry, in particular, is widely used in clinical laboratory settings. Flow cytometry is particularly useful in measurement of subsets of interest within a complex population of cells. For example, U.S. Pat. No. 4,727,020 to Recktenwald describes the use of two fluorescent channels to detect cells in a subpopulation specifically labeled with two different immunofluorescent agents. U.S. Pat. No. 4,284,412 to Hansen, et al. describes the use of fluorescence channels to detect forward and right angle light scatter of cells of different subpopulations in blood. Major disadvantages of flow cytometry are that it requires complex and expensive equipment, each sample must be run and analyzed individually and the results require interpretation and are frequently not repeatable. These disadvantages are particularly acute in a clinical laboratory which must process multiple patient specimens daily and where the need for consistent and reliable results is extremely important.

U.S. Pat. No. 5,385,822 to Melnicoff et. al. and U.S. Pat. No. 5,374,531 to Jensen disclose alternative methods to flow cytometry for counting the number of lymphocytes or of a subset of lymphocytes within a mixed population of cells. The methods described in these patents involve coupling a detectable reporter substance to the bio-membrane or incorporating the reporter substance into the cell, then separating the subset or population of interest and detecting the reporter substance. These methods utilize affinity separation to isolate populations of interest from a complex mixture of cells. This technique offers improvements over flow cytometry but it is still based on cell counting techniques.

The major difficulty with all cell counting techniques is that they do not measure the function of specific cells or their responses to specific antigens or mitogens. Cells that respond to mitogens or antigens have unique cell surface markers found only on the responding cells. Methods for counting the number of cells exhibiting these markers have been described but these methods are relatively insensitive due to the fact that the responding cells are generally a small fraction of the total population. These methods are also tedious and subject to poor reproducibility.

Direct measurement of responses of lymphocytes have included lymphoproliferation assays, cytotoxicity assays, and measurement of cytokines. In general, these methods require separation of white cells from the original sample followed by incubation with antigen or mitogen. Measurement of the function of specific subsets of lymphocytes requires extensive manipulations prior to the assay. The requirement for antigen presenting cells then means that additional cells have to be added back to the culture. Lymphoproliferation assays are based on division of responding cells and are typically performed using radioactive isotopes. Because they evaluate the division of a small population of cells and require tissue culture, the assays take 3–10 days and are subject to significant variability based on the specific technique and the reagents used in the assay. Cytotoxic tests also require significant cell manipulation and are similarly highly variable depending on the specific conditions used. Cytokine assays can also be performed, but require many steps and separation of subsets of interest prior to stimulating the cells. U.S. Pat. No. 5,344,755 to McMicheals describes a modification of the cytotoxic assay based on initial immunomagnetic separation of T lymphocytes, but this method still requires extensive manipulation of effector cells. U.S. Pat. No. 5,344,755 provides an example of use of cytokine measurements to assess immune status in HIV positive patients but is tedious and requires multiple steps. These methods have required separation of critical cell types, long incubation times, and in some cases use of radioactive substances. For these reasons, these methods have not been suitable for clinical applications.

Affinity separation of cells using protein-coated magnetic particles or other types of solid supports such as polystyrene particles is known and is used as part of several of the methods cited above, see U.S. Pat. Nos 5,374,531, 5,385,822, and 5,344,755. Various methods for sorting biological populations via affinity separations on solid supports have been described in the patent literature and elsewhere. See, for example, U.S. Pat. Nos. 3,970,518, 4,710,472, 4,677,067, 4,666,595, 4,230,685, 4,219,411, 4,157,323; see also, E. T. Menz, et al., Am. Biotech. Lab. (1986); J. S. Kemshead et al., Molec. Cell. Biochem., 67:11–18 (1985); T. Leivestag et al., Tissue Antigens, 28:46–52 (1986); and J. S. Berman et al., J. Immunol., 138: 2100–03 (1987). In performing such methods, a binding molecule (e.g., monoclonal antibody) is typically conjugated to the solid supports such as the magnetic particles or plastic beads, and added to a test sample under conditions causing binding to a characteristic determinant on the analyte of interest. The cells complexed with the solid support are then separated from the uncomplexed cells by exposure to a magnetic field or filtration or other method depending on the nature of the solid support. The use of this technology to separate certain subpopulations of lymphocytes from bone marrow cells prior to transplantation and to eliminate post-transplantation graft vs. host reaction, has also been reported. See A. Butturini et al., Prog. Bone Marrow Transpl. 4:13–22 (1987). Other reported uses of this technology include the separation of tumor cells (see: Kemshead et al., B. J. Cancer 54:771–78 (1986)) and the separation of lymphocyte subpopulations for subsequent functional evaluation.

The problems that arise when the lymphocytes are first separated by magnetic or other solid phase affinity techniques and then used for functional assays, are that the interaction of the lymphocyte with the binding molecule can itself induce functional changes in the lymphocyte that may obscure later changes that are to be measured. In addition, the accessory cells required for response of the T cells may no longer be present especially if a specific subset of cells are isolated. In addition, isolated cells are removed from the native environment and it is difficult to maintain the sterility of the sample required for further tissue culture.

SUMMARY OF THE INVENTION

The subject invention provides a convenient, reliable, and relatively rapid method for analyzing the function of various sets or subsets of lymphocytes. The method of the invention involves incubating a population of cells with a mitogen or antigen, separating the desired subset of cells by means of the interaction of a specific binding reagent that is attached to the solid phase with a cell surface determinant that is present on the cell subset of interest, lysing of the separated cells, and measuring an intracellular component that is increased if the cells have responded to the stimulus.

In an advantageous embodiment of the invention, the functional activity of a set or subset of lymphocytes which is distinguished by a characteristic cell surface determinant and which is contained within a mixed cell population, is measured by: exposing the sample to a mitogen or antigen, incubating the sample for a period of time, binding the set or subset of lymphocytes to a solid support through the interaction of the cell surface determinant and a specific binding substance which is linked to the solid support, washing the cells to remove any unbound cells as well as potentially interfering substances in the media, lysing the cells, and detecting the ATP in the solution. The results obtained can be compared against a known standard. Alternatively, the sample can be divided into two or more parts with at least one of the parts being incubated without addition of any stimulant, while the second part is incubated with addition of an antigen or mitogen.

One aspect of the invention is the determination of the response of lymphocytes to a mitogen. In this case, the response of a set of lymphocytes to a mitogen is a general measure of immune function. This application is of particular significance in the measurement of the effects of immunosuppressive drugs or agents. In this case, the responsiveness of an entire set of lymphocytes such as the T lymphocytes can be determined. Alternatively, the effect of a virus such as HIV can be assessed by evaluating the response to mitogens of a subset of T lymphocytes that express the CD4 cell surface determinant.

Another aspect of the invention is the determination of the response of lymphocytes to antigens that might include infectious agents, drugs, chemicals, autoantigens, or tumor antigens. This aspect of the invention is particularly important in monitoring the exposure of an individual to an infectious disease or an agent or to diagnosis of hypersensitivity, autoimmune disease or cancer. This aspect of the invention is also useful in monitoring vaccine efficacy and in assessment of immunotoxicity of chemicals, drugs, and industrial compounds.

Another aspect of the invention is that the response of T lymphocytes from various subsets including functional or differentiation based subsets to a mitogen or antigen can be assessed based on the expression of different determinants specific for a functional, differentiation, or activation marker on the cell surface. In this aspect of the invention, an antigen is added to a sample and incubated for a period of time. Following the incubation, the cell subset of interest is isolated by binding the cells to a solid support through a determinant on the cell surface. The cells are washed and lysed, and the level of an intracellular component that increases as a result of the activation is measured.

The method of the invention is highly sensitive due to the measurement of an intracellular component whose level increases rapidly following lymphocyte exposure to mitogen or antigen, for example ATP, other metabolic intermediates such as NADP, or proteins involved in cell cycle regulation such as PCNA. In an advantageous embodiment, the level of ATP is measured utilizing the bioluminescent reaction of luciferin:luciferase. Bioluminescent measurement of ATP is a highly sensitive measure.

A further aspect of the invention is that the total time required for the method is generally 6–72 hours and typically 18–24 hours. The relatively short time period is an advantage in comparison to the current methods which requires 3–10 days to complete.

In one embodiment of the invention, test kits are provided for performing the methods of the invention. Test kits typically contain the antigen or mitogen, the solid state with appropriate binding substance, the reagents required for detection of ATP levels, appropriate diluent and wash solutions, standards or instructions for preparing the same, and optionally, other accessories such as test tubes, magnetic separators, washers, and transfer pipettes, which are useful in carrying out the methods of the invention.

DETAILED DESCRIPTION OF THE INVENTION

Figure 1:
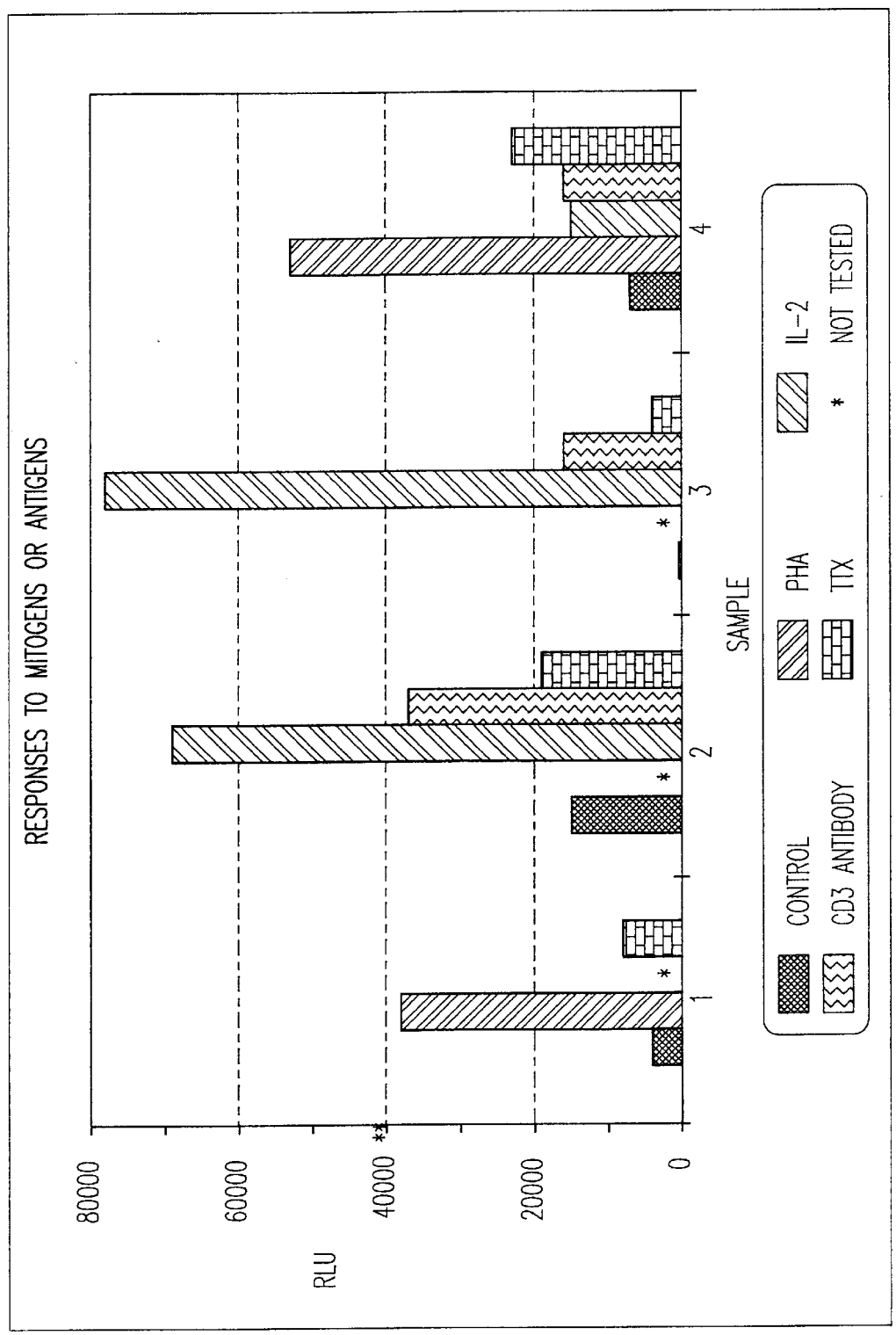
FIG. 1 shows the response of different patient samples to mitogens and antigens of Example 2 and demonstrates the ability of the methods of the invention to detect responses to mitogens and antigens in individual patient samples.

The present invention provides sensitive and efficient methods for measuring the responsiveness of a set or subset of lymphocytes (e.g., T cells or B cells) distinguished by some characteristic determinant expressed on the cell surface within a mixed cell population. In particular, the invention provides a method for measuring the response of lymphocytes to inducing agents including mitogens or antigens.

The current invention circumvents the problems of the prior art by separating the T cells from the sample after the cells are exposed to the antigen and in a time frame in which the interaction of the lymphocyte with the binding molecule on the beads will not affect the results.

A second distinguishing aspect of the invention involves the measurement of the levels of ATP in the cells following the separation of the subset of interest. It is well known that ATP levels are indicative of metabolic activity. See, for example, Kangas et al, Med. Biol. 62:338–43 (1984) and Lundin et al. Meth. Enzymol. 133:27–42. Measurement of ATP levels have been used in studies of chemotherapeutic drugs and other agents of cell lines and have been used to monitor increases in biomass and cell number. ATP levels can be measured very sensitively using the bioluminescent reaction of firefly luciferase with luciferin. See, for example, Leach and Webster, Meth. Enzymol. 133:51–70, (1986). A number of methods for assessing ATP levels in bacteria or in somatic cells have been reported. See, for example, U.S. Pat. Nos. 3,690,832, 5,283,179, 4,144,134, 4,283,490, 4,303,752 each of which is hereby incorporated by reference. What has not been appreciated in the prior art is that as a result of the response of T cells to a mitogen or antigen, the metabolic activity of the cell that responds increases significantly and that this increase is reflected in significant increases in the level of ATP levels. Further, small changes in ATP levels or changes in ATP levels in a small number of cells can be measured due to the sensitivity of the luciferin:luciferase system.

The invention addresses a major existing need for improved methods to measure the responsiveness of T lymphocytes to mitogens and antigens, i.e. T cell function. These methods exhibit sensitivity comparable to or greater than methods heretofore available. These methods also permit the user to analyze multiple samples in a relatively brief time, and eliminate the need for expensive equipment and highly skilled personnel to perform the method, and do not use radioactive materials.

The methods of the invention can be used as an adjunct to or a replacement for methods and tests performed in the clinical laboratories to count the number of lymphocytes in different subpopulations. The methods described herein incorporate the required sensitivity of assays that take much longer time with the shortened time frame of cell counting assays. The utilization of standards and the provision of test kits based on this methods incorporating all the necessary reagents results in increased reproducibility and consistency required for tests used in the clinical laboratory.

The methods of the invention have several advantages over current methods. The time required for response is significantly less than for other assays. The provision of all the materials required for the assay in a test kit and the simplicity of the nature of the measurement results in consistency in results from lab to lab. Further, multiple samples can be run simultaneously. The methods are simple, rapid, sensitive, and applicable to the clinical laboratory setting.

Inducing Agents

In the context of this invention, inducing agents are substances that interact with lymphocytes such that the result of the interaction is a change in the state of the cell. In particular, "inducing agents" refer to substances that cause resting lymphocytes to become activated and that can also induce functional activity in the cell. In general, inducing agents fall into two classes: (i) mitogens are inducing agents that interact with all the lymphocytes of a particular subset and induce activation followed by proliferation in the responding cells and (ii) antigens that interact through specific receptors on limited subpopulations of cells.

Mitogens for different populations of lymphocytes are known and include lectins, antibodies directed against certain lymphocyte cell surface receptors such as CD3 for T lymphocytes or CD2 for B lymphocytes, growth factors and lymphokines, phorbol esters, and other biochemical substances that are known to those versed in the art. Advantageous mitogens include phytohemagluttinin (PHA), Con A, or monoclonal antibody to CD3.

Antigens react with a smaller subset of lymphocytes through specific receptors on the cell surface. Each lymphocyte has on its cell surface a receptor for a specific antigen or molecule. For B lymphocytes, the cell surface receptor is antibody that is membrane bound. For T lymphocytes, the cell surface receptor is the T cell receptor with recognized antigen that is presented in the context of major histocompibility molecules on the surface of another cell. The response of the immune system to specific foreign invaders is based on the recognition of antigens by the receptors on the cell surface of these cells and the resultant functional activation that occurs as a result of this interaction. In general, the antigens that are bound to these cell surface receptors are small parts of larger molecules and can include parts of infectious agents, such as viruses, bacteria, fungi, and the like, drugs, organic chemicals, and inorganic chemicals such as silicone, metals such as beryllium, and proteins such as tumor cell proteins, or proteins derived from implanted or transplanted organs. Advantageous antigens include gp 120 protein or peptides from gp 120 of HIV virus envelope glycoprotein, outer surface proteins from bacteria such as OSPA, B or C from Borrelia burgdorferi, $SiO_2$, disrupted inactivated Q fever cells, PPD, or tetanus toxoid.

Target Lymphocytes

The cell subsets of interest are present in test samples or specimens of varying origin including biological fluids such as whole blood, urine, stool, saliva, cerebrospinal fluid, amniotic fluids, tissue extracts, lavage fluids, tumor biopsies, transplant biopsies or they can be from culture. Cells of interest are of human or animal origin. Samples also include specimens from various biological origins that have been partially purified by density gradient centrifugation or other separation methods that are used to isolate partially purified samples of cells.

In analyzing a sample containing a cell subset of interest according to the method of the invention, the cell population suspended in its natural biological fluid or in a suitable biological or synthetic medium, is initially exposed to the mitogen or specific antigen of interest. It is a particular aspect of the invention that the exposure occurs for a relatively short period of time. Depending on the nature of the antigen or mitogen being examined, the time period of exposure is 6–72 hours or longer, but is usually of 24 hour duration.

Of particular interest in diagnostic, therapeutic, and research purposes are measurement of the responses of T lymphocytes and lymphocyte subsets, including major functional subsets such as T helper cells and suppressor/cytotoxic cells to mitogens or to specific antigens. Quantitation of the responsiveness of a specific subset of T lymphocytes is important in certain physiological conditions. For example, individuals infected with human immunodeficiency virus lose responsiveness in the CD4 cell population to both mitogens and antigens prior to loss of activity in other cell subsets. Likewise, responsiveness of subclasses of T cells to mitogens is important in monitoring individuals that are potentially immunosuppressed due to chronic stress, chemotherapy, or drug treatment. Quantitation of the responsiveness of a subset of lymphocytes to specific antigens is important in measuring the individual's exposure to an infectious agents or to a drug or compound or to determine a hypersensitivity reaction to a drug or chemical. In addition to the major functional subsets other cells subsets of interest include cells at different stages of differentiation or cells at different time points after initial interaction with a mitogen or antigen.

Characteristic Determinants

The functional subsets of interest are distinguished by expression of characteristic cell surface determinants. In addition, cells from the same subset but at different stages of differentiation are distinguished by expression of characteristic determinants on the cell surface. Cells with different functional activity or at different times after the initial interaction with a mitogen or antigen can also express different cell surface determinants.

In this invention, characteristic determinant denotes an element that identifies or determines the nature of something. When used in reference to the methods of the invention, "determinant" means a molecule expressed on the cell surface that characterizes the cell in some fashion. Cell-associated determinants include, for example, components of the cell membrane, such as membrane bound proteins or glycoproteins or lipids or glycolipids and including cell surface antigens of either host cell or viral origin, histocompatibilty antigens, or membrane receptors. Particular characteristic determinants within the scope of this invention include CD69, CD25, CD26, CD27, CD28, CD71, and MHC Class II antigens.

A determinant is the portion of the cell that interacts with a specific binding substance. Cells are separated by means of the specific interactions between determinants on the cell surface and specific binding substances that are attached to solid phases. This process is referred to herein as "affinity separation." Specific binding substances that may interact with cell surface determinants include antibodies capable of recognizing the determinants.

Binding Substances

Determination of the presence or quantity of cell subsets according to the methods of the invention is accomplished by the selective interaction between cells of the subset of interest and a specific binding substance. The specific binding substance used in the practice of this invention must exhibit selective recognition for the characteristic cellular determinant. In analyzing a mixed cell population for a subpopulation and/or subset having a characteristic cell surface antigen, for example, the specific binding substance can be the complementary antibody that immunospecifically recognizes the antigen of interest. Based on such selective recognition, the specific binding substance is capable of selective interaction and binding with the subset of interest to form complexes or aggregates which are physically or chemically separate from the test medium and other components therein which are not of interest. In one advantageous embodiment, blood specimens containing T lymphocytes and monocytes bearing the surface antigen CD4 are exposed to a specific binding substance comprising a CD4 monoclonal antibody.

The term "antibodies" as used herein includes monoclonal or polyclonal immunoglobulins and immunoreactive immunoglobulin fragments. Other types of specific binding substances include lectins, hormones, cytokines, receptor ligands, etc.

Monoclonal antibodies to particular cell surface determinants are of particular importance in this embodiment of the invention. For example, lymphocytes, which comprise a subpopulation of whole blood, can be selected by a monoclonal antibody which is directed against a leukocyte surface antigen. The CD45 antigen is uniformly expressed on all lymphocytes; however, the CD45 antigen is also expressed on monocytes. Therefore, if selective binding of lymphocytes is desired, it is necessary to select a CD45 monoclonal antibody which binds to significantly more binding sites per cell on lymphocytes than monocytes or that binds with higher strength to lymphocytes than to monocytes.

In a particularly advantageous embodiment, it is desirable to separate only T helper lymphocytes within a sample of whole blood. This is accomplished as described above, using monoclonal antibodies directed against the T cell surface antigens, such as CD4 or is accomplished using a combination of antibodies that react primarily with T helper lymphocytes. In another embodiment of the invention, lymphocytes that have been activated by exposure to specific antigen are separated by utilizing antibodies directed against antigens that are expressed only following activation on the cell surface. These antibodies react with one or a combination of the following cell surface antigens, CD25, CD69, CD71, CD45RO, or MHC Class II antigens. Using these antigens for separation results in a significant amplification of the signal from the assay since only the cells that express these markers have responded to the signal from antigen or mitogen.

Specific binding substances are conveniently affixed to a solid phase or insoluble fluid phase to facilitate separation from the test medium. A variety of solid support materials can be used e.g., polystyrene, nylon or agarose beads, and are well known to those skilled in the art. In a particularly advantageous embodiment of the invention, the specific binding substance is affixed to a plurality of magnetic beads, which comprise ferromagnetic, paramagnetic or diamagnetic material. Techniques for attaching the specific binding substance to the beads are known to those skilled in the art. Suitable techniques include cross-linking, covalent binding, or physical absorption. Alternatively, a non-solid phase, primary specific binding substance is used in conjunction with a second or auxiliary specific binding substance which is capable of interacting selectively with the primary specific binding substance, and which is affixed to a solid phase. Representative primary and auxiliary specific binding substances useful for this purpose are: soluble murine antibody/Protein A affixed to a solid phase; soluble murine antibody/anti-mouse immunoglobulin raised in another species and affixed to a solid phase; biotinylated antibody/avidin affixed to a solid phase.

In the case where the sample being tested is derived from culture or is separated by density gradient separation prior to separation on a solid support, a simple separation procedure is sufficient to separate the subset of lymphocytes of interest from the rest of the cell population. In the case of more complex samples such as whole blood it is necessary at times to wash the complex to remove cells that are trapped or bound nonspecifically. A variety of solutions (e.g., 0.15M ammonium chloride, 1.0M potassium carbonate, 0.1M EDTA, pH 7.2) that specifically lyse red blood cells, platelets, or other potential contaminants are known to those versed in the art. In addition, solutions that contain other substances such as proteins, sugars, or salts or that are of specific pH values can be useful in reducing the nonspecific binding of other cell types or in eliminating or lysing cell types that are separate from those of interest (e.g., solution of Hank's buffered saline containing 10% of FCS is particularly useful). Upon separation and following washing, if necessary, the media is removed from the complex.

Lysis

Following separation of the cells of interest, the separated cell population is lysed by the addition of a solution containing substances that can lyse lymphocytes. A variety of such solutions exist and are well known to those in the art. These solutions include distilled water, solutions containing detergents such as Triton-X or NP-40, and buffered solution such as HEPES containing 0.1M benzalkonium chloride, pH 7.4. It is important that the material and the solution chosen do not interfere with the system for measuring ATP, do not contain ATP, and do not degrade ATP.

It is a significant feature of the invention that the time from the exposure of the sample until the time that the cells are lysed is minimal, usually less than 2 hours preferably less than 1 hour. This is significant because interaction of lymphocytes with many antibodies against cell surface antigens can result in a response. This has been a significant problem in determining the function of specific cell types as the isolation of the cell type can induce cell activation.

Measurement of ATP Levels

Following lysis of the cells, the level of ATP in the solution is measured. In an advantageous embodiment, the ATP is measured by the addition of a solution containing firefly luciferase and luciferin in the presence of magnesium ions. ATP can also be measured by other means including immunochemical or biochemical reaction systems.

The measurement of an intrinsic component of the cell is important because it eliminates an additional step as well as the intrinsic variability of any labeling process. Increased ATP has been used as a marker of increased cell mass, but has been relatively insensitive because all the cells in the population exhibit a baseline level of ATP. The subject invention works because the measurement of ATP is made following separation of the cell population of interest.

Kits

According to another aspect of the invention, the different reagents, together with the various accessories used in practicing the methods of the invention, including media for dilutions, solid supports for immobilizing cells, lysis reagents, antigens or mitogens, and wash buffers, one or more standards, or instructions for the preparation thereof are conveniently packaged in a test kit. The reagents included in the test kit may take various forms and are packaged dry together with appropriate diluents or may be supplied in ready to use form.

In accordance with the methods of the present invention, kits for evaluating the T cells responses are envisioned. In particular, the invention includes a kit containing antigens or mitogens either in liquid or lyophilized form, paramagnetic beads coupled with an antibody for isolation of the predetermined subset of cells, cell culture media for dilution of samples, wash buffer for washing complexes, and associated reagents for performing the assay.

The following examples are provided to describe the invention in further detail. These examples are intended to illustrate specific applications of the methods of the invention and should in no way be construed as limiting the invention.

EXAMPLES

Example 1

Detection of Mitogen Responsiveness of CD4 positive T Lymphocytes Useful for Measuring Immune Function in HIV infection, in Response to Stress, or Following Chemotherapy.

Peripheral blood mononuclear cells were isolated from source leukocytes (Gulf Coast Blood Bank) originally obtained from the peripheral blood of normal individuals by gradient centrifugation over Ficoll-Hypaque. Cells from the buffy layer were rinsed by centrifugation in RPMI containing 10% fetal calf serum (FCS) and were adjusted to a cell density of approximately $1 \times 10^5$ cells/ml with RPMI containing 5% fetal calf serum (FCS). One aliquot of cells was cultured unstimulated while a second aliquot of cells was stimulated with phytohemagglutinin (PHA), a T cell mitogen at a concentration of 1 $\mu$g/ml for 24 hours. The aliquots were diluted 1:20 with RPMI 1640 containing 10% FBS. Antibody to CD4 at a concentration of 2 $\mu$g/ml was added to all cultures. Cells were incubated at room temperature for 30 minutes, then 100 $\mu$l of paramagnetic beads coated with goat anti-mouse antibody (obtained from Advanced Magnetics) was added. The cell suspension was gently mixed and incubated for 30 minutes at room temperature. The cells and beads were resuspended then placed next to a permanent magnet that was placed such that the magnetic field was in a direction perpendicular to gravity. After the beads formed a dense pellet, the media was aspirated and the magnet removed. Additional buffer was added and the cells and beads were resuspended. This process was repeated several times. After fully removing the media, the cells in the bead pellet were lysed with a detergent solution identified as somatic cell lysis reagent (Sigma) and the tube is placed into the luminometer. One hundred microliters of a mixture containing luciferin, luciferase, and Mg2+ in a solution containing 0.25 mM hepes, 0.1 mM DTT, and 0.5% BSA was injected into the tube and the counts were determined.

Negative controls consisting of lysis buffer only or cells that are incubated with nonspecific beads, i.e., beads coated with a different isotype from that of the primary antibody were also tested. Finally, an ATP standard was run in each assay to confirm that the luciferin:luciferase reaction was occurring at appropriate levels. Table 1 below shows the results obtained

TABLE 1

Response of PBMC separated using CD4 Antibody and Goat anti-Mouse Paramagnetic Beads.

| Treatment | Relative Light Units |
|---|---|
| Blank (No Beads) | 1265 |
| ATP Control | 420,653 |
| Unstimulated | 8768 |
| PHA Stimulated | 38903 |
| Uncoated Beads | 1050 |

Example 2

Measurement of the Response of CD4 positive T lymphocytes to Mitogens, Cytokines and to a Toxin Antigen.

Peripheral blood mononuclear cells were isolated from several different individuals by gradient centrifugation, washed, and cultured in RPMI 1640 containing 5% FCS. The cells were aliquoted and left either unstimulated or stimulated with PHA, CD3 antibody, tetanus toxoid, or influenza viral antigen. All samples were not incubated with the same antigens. Following a 48 hour incubation the cells were diluted with RPMI 1640, incubated with mouse monoclonal antibody to CD4 antigen for 30 minutes at room temperature, then incubated with goat antibody to mouse IgG conjugated to paramagnetic beads (Advanced Magnetics, Inc.) for 30 minutes at room temperature. Following separation using a permanent magnet and washing of the sample, the cells were lysed using somatic cell lysing reagent (Sigma Chemical). Luciferin/luciferase reagent (Sigma Chemical) was diluted 1:10 and 100 µl was added. Relative light units were determined. FIG. 1 shows the response of different patient samples to these mitogens and antigens and demonstrates the ability of the methods of the invention to detect responses to mitogens and antigens in individual patient samples.

Example 3

Comparison of Results Obtained after PHA Stimulation of T lymphocytes Separated by CD4, CD69, or CD3.

Figure 2:
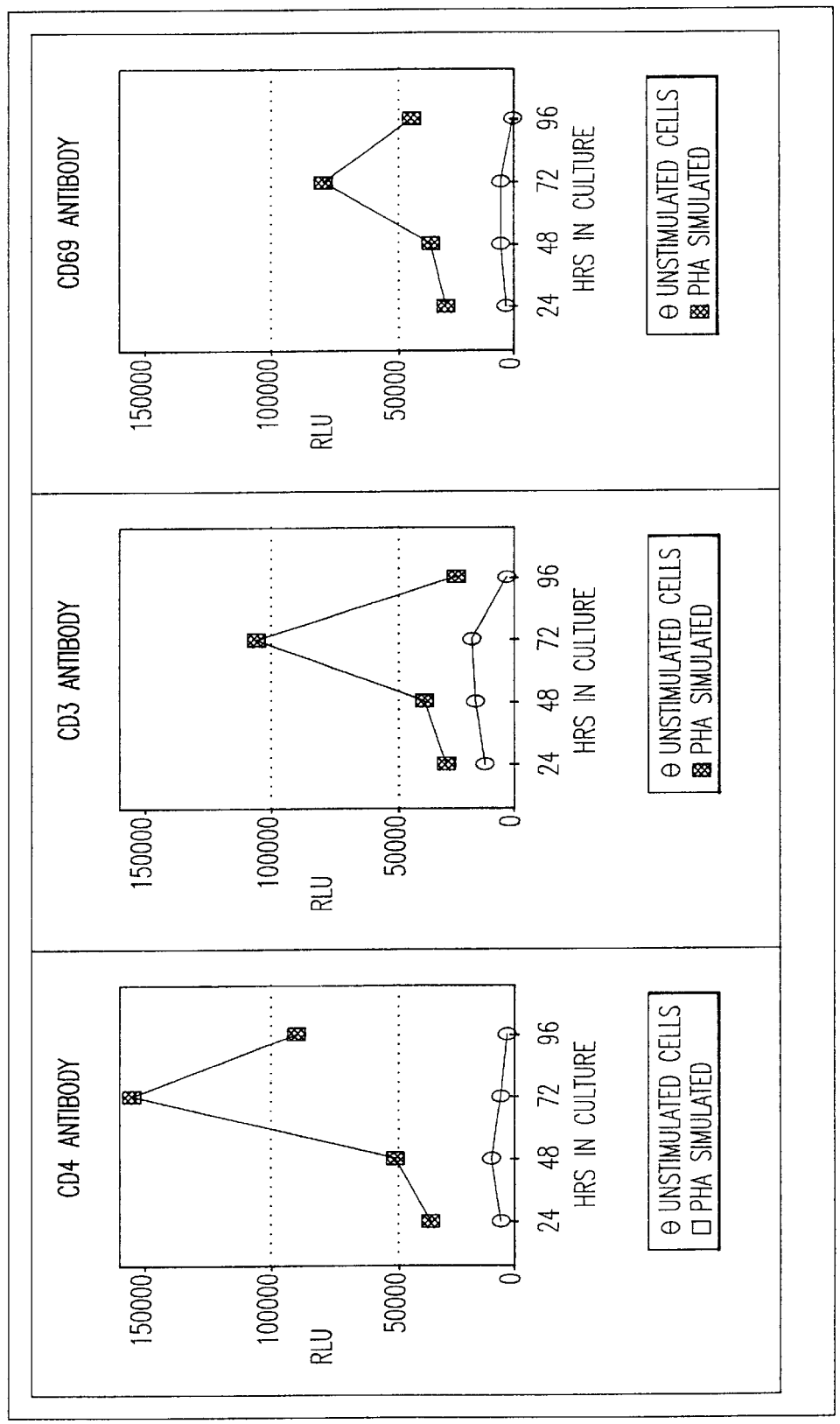
FIG. 2 shows the results of the assays of Example 3.

This Example examines the ability of the assay to be performed using different cell surface markers. Peripheral mononuclear cells were either unstimulated or stimulated with PHA (1%) for 24, 48, 72, or 96 hours. Aliquots of the unsimulated cells or the PHA stimulated cells were incubated with mouse monoclonal antibody to CD3, the T cell receptor, CD4, or CD69 for 30 minutes at room temperature. All aliquots were then incubated with paramagnetic beads onto which had been adsorbed goat anti-mouse IgG for 30 minutes at room temperature. The beads and cell complexes were separated using a permanent magnet and washed three times with RPMI containing 10% FCS . The cells were lysed with a 0.5% NP-40 solution. Luciferin:luciferase mixture (Sigma Chemical Company) was diluted 1:10 and 100 µl added to each tube. FIG. 2 shows the results of these assays. In all cases, the relative light units from the stimulated cells were greater than those from the unstimulated cells. This demonstrates the use of different cell surface markers to evaluate the response of lymphocytes from different subsets.

Example 4

Measurement of the Response of T Lymphocytes to a Bacterial Antigen.

Balb/c mice were immunized with a total of 100 µg of Q fever antigen prepared from Nine mile strain (Integrated Diagnostics, Inc.) emulsified in complete Freund's adjuvant. Prebleeds were taken from the orbital sinus of 10 mice. Additional bleeds were obtained at 7 days post inoculation. Approximately 100–200 ml of blood were obtained from each mouse. Peripheral blood mononuclear cells were prepared by density gradient centrifugation. White cell layer was removed and washed with RPMI-1640 containing 10% FCS. Approximately 100 µl of cells were placed in each tube. The cell pellets were cultured either without any other additions or in the presence of Q fever antigen (10 µg/ml or 1 µg/ml). After 24 hours, the cultures were diluted 1:10 with RPMI-1640 containing 10% FCS and 100 µl of super paramagnetic beads coated with antibody to mouse CD4 (Advanced Magnetics, Inc.) were added. The beads and cells were incubated at room temperature for 30 minutes. The beads together with any complexed cells were separated using a permanent magnetic and washed 3 times in RPMI containing 10% FCS. The cells were lysed by adding 100 µl of Somatic Cell Lysing Reagent (Sigma Chemical Co.). After an additional 10 minutes at room temperature, 100 µl of a luciferase: luciferin reaction mixture (Sigma Chemical Co.) was injected and the light output determined by a luminometer.

In the prebleeds from the mice, samples incubated with Q fever antigen gave signals that were identical to those incubated without Q fever antigen. The following table shows the results from samples obtained at 7 days following injection of the antigen. There was a dose dependent response of T cells detected.

TABLE 2

T cell response to Q fever antigen in mouse injected with antigen.

| | Total RLU | Index |
|---|---|---|
| Control | 8447 | — |
| Q Antigen 10 ug/ml | 22346 | 2.6 |
| Q Antigen 1 ug/ml | 16566 | 2.0 |

Example 5

Measurement of the Response of T Lymphocytes Using Whole Blood as a Sample.

Blood samples were obtained from normal donors and collected in heparin as an anti-coagulant. Aliquots of the blood (100 µl) were diluted 1:5 with RPMI 1640. Replicates received either no addition, PHA at 1%, or IL-2 at 100 U/ml final concentration. Samples were incubated overnight at 37° C. The following day 100 µl of the samples were removed, incubated with mouse monoclonal antibody to CD4 antigen for 30 minutes at 37° C. Paramagnetic beads coated with goat anti-mouse IgG were added to each sample (100 ul) and incubated for 30 minutes at 37° C. The bead:cell complexes were isolated from the samples using a permanent magnetic and the complexes were washed three times with PBS containing 10% FCS and 0.1% BSA. Cells were lysed using distilled water. Luciferin:luciferase was added and the relative light units determined. The following table shows the results.

TABLE 3

Measurement of T cell response to mitogens in a whole blood sample

| Treatment | Relative Light Units |
|---|---|
| Control | 458,451 |
| PHA | 5,836,682 |
| IL-2 | 2,632,415 |

Example 6

Measurement of the Responses of CD8 Positive T Lymphocytes to a Viral Antigen.

Peripheral blood mononuclear cells were isolated from heparinized whole blood from normal blood donors by gradient density centrifugation. Cells were washed in RPMI containing 10% FCS and resuspended in this media at a density of 1×105 cells/ml and aliquoted. Replicates received either no additions or different levels of influenza A antigen or PHA. After 24 hours, a mouse monoclonal antibody to CD8 was added and the cells were incubated for 30 minutes at room temperature. Paramagnetic beads coupled to goat antibody to mouse IgG were added and the complexes were separated by placing the cultures next to a permanent magnet. Complexes were washed three times with PBS containing 10% FCS then the cells were lysed by adding 0.05% Triton X 100 in PBS. ATP levels were determined using luciferin:luciferase. All individuals showed responses to PHA with stimulation indexes of >10, while the range of stimulation indexes to influenza viral antigens ranges from 1.2–4.0.

It is understood that the examples and embodiments described herein are for illustrative purposes only and that various modifications of changes in light thereof will be suggested to persons skilled in the art and are to be included within the purview of this application and the scope of the appended claims.

What is claimed is:

1. A method for rapidly analyzing lymphocytes for lymphocyte activation comprising the steps of:

incubating a sample containing a mixed population of cell types including a plurality of subsets of lyphocytes where each subset includes lymphocytes with characteristic determinants that distinguish one subset from another, with an inducing agent selected from the group consisting of mitogens and antigens; then separating a selected subset of lymphocytes from said sample; then lysing lymphocytes in said selected subset to release an intracellular component selected from the group consisting of ATP, NADP, and PCNA; then detecting a level of said intracellular component; and assessing lymphocyte activation for said selected subset of lymphocytes from said level of intracellular component detected in said detecting step, wherein the total time required for performing all steps is 6–24 hours.

2. A method as recited in claim 1 wherein said step of separating comprises the steps of contacting said sample with a solid support having a specific binding substance, said specific binding substance being specific for at least one characteristic determinant of said selected subset of lymphocytes, said contacting step resulting in the formation of a complex of cells, binding substance and solid support; and removing said complex from a remainder of said sample.

3. A method according to claim 1 wherein said inducing agent is a mitogen.

4. A method according to claim 1 wherein said inducing agent is an antigen selected from the group consisting of viruses, bacteria and fungi.

5. A method as in claim 4 where said antigen is a virus or a bacteria or a subcomponent thereof selected from the group consisting of O fever cells, PPD, tetanus toxoid, OSPA, OSPB, OSPC, gp 120 protein, and peptides derived from gp 120.

6. A method according to claim 1 wherein said inducing agent is selected from the group consisting of drugs, organic chemicals, inorganic chemicals, metals, tumor cell proteins, and proteins derived from transplanted organisms.

7. A method according to claim 1 wherein said subset of lymphocytes is selected from the group consisting of T lymphocytes, helper T lymphocytes, natural killer T lymphocytes, and cytotoxic T lymphocytes.

8. A method according to claim 2 wherein said characteristic determinant is a characteristic determinant of T cells and is selected from the group consisting of a functional marker, a marker of a particular differentiation stage, and an activation marker.

9. A method according to claim 2, wherein said solid support comprises magnetic or paramagnetic material.

10. A method as recited in claim 9 wherein the step of separating said complex is performed by magnetic separation.

11. A method according to claim 2, wherein said solid support comprises polystyrene.

12. A method according to claim 2 wherein said detecting step includes the step of adding luciferin to said intracellular component released from said lymphocytes in said subset of lymphocytes.

13. A method according to claim 2, wherein the said specific binding substance is an antibody.

14. A method according to claim 2, wherein said specific binding substance is a cytokine.

15. A method according to claim 1 wherein said intracellular component is ATP, and further comprising the steps of determining a level of ATP in a control sample and comparing the level of ATP in the level of ATP identified in said detecting step.

16. A method according to claim 15 wherein said standard sample is liposomes containing ATP.

17. A method according to claim 1 wherein said subset of lymphocytes are B lymphocytes.

18. The method of claim 1 wherein said intracellular component is ATP.

19. The method of claim 1 further comprising the step of selecting said sample to be whole blood.

* * * * *